United States Patent [19]
Palmer

[11] Patent Number: 6,027,522
[45] Date of Patent: Feb. 22, 2000

[54] SURGICAL INSTRUMENT WITH A ROTATABLE DISTAL END

[75] Inventor: Matthew Palmer, Miami, Fla.

[73] Assignee: Boston Scientific Corporation, Natick, Mass.

[21] Appl. No.: 09/089,127

[22] Filed: Jun. 2, 1998

[51] Int. Cl.[7] .................................................. A61B 17/28
[52] U.S. Cl. ..................... 606/205; 606/206; 606/207
[58] Field of Search ..................... 606/205, 206, 606/207, 208, 170–175; 128/751–755

[56] References Cited

U.S. PATENT DOCUMENTS

| | | |
|---|---|---|
| 5,133,727 | 7/1992 | Bales et al. . |
| 5,141,519 | 8/1992 | Smith et al. . |
| 5,171,258 | 12/1992 | Bales et al. . |
| 5,439,478 | 8/1995 | Palmer ..................................... 606/205 |
| 5,542,432 | 8/1996 | Slater et al. ............................. 128/751 |
| 5,569,243 | 10/1996 | Kortenbach et al. ...................... 606/46 |

*Primary Examiner*—Michael Buiz
*Assistant Examiner*—Lien Ngo
*Attorney, Agent, or Firm*—Finnegan, Henderson, Farabow, Garrett & Dunner, L.L.P.

[57] ABSTRACT

A rotatable surgical instrument for use alone or in conjunction with other instruments such as an endoscope. The instrument, having a proximal end and a distal end, includes a proximal actuator assembly, a distal end effector assembly having a surgical tool and a first rotational engagement member, a hollow member extending between the actuator and the end effector assembly, and a control member extending through the hollow member. The control member has a proximal end connected to the actuator assembly, a distal end connected to the end effector assembly, and a second rotational engagement member. In operation, actuation of the actuator assembly causes the control member to actuate the surgical tool, and the first engagement member engages the second engagement member to transmit torque applied to the control member to the end effector assembly.

35 Claims, 5 Drawing Sheets

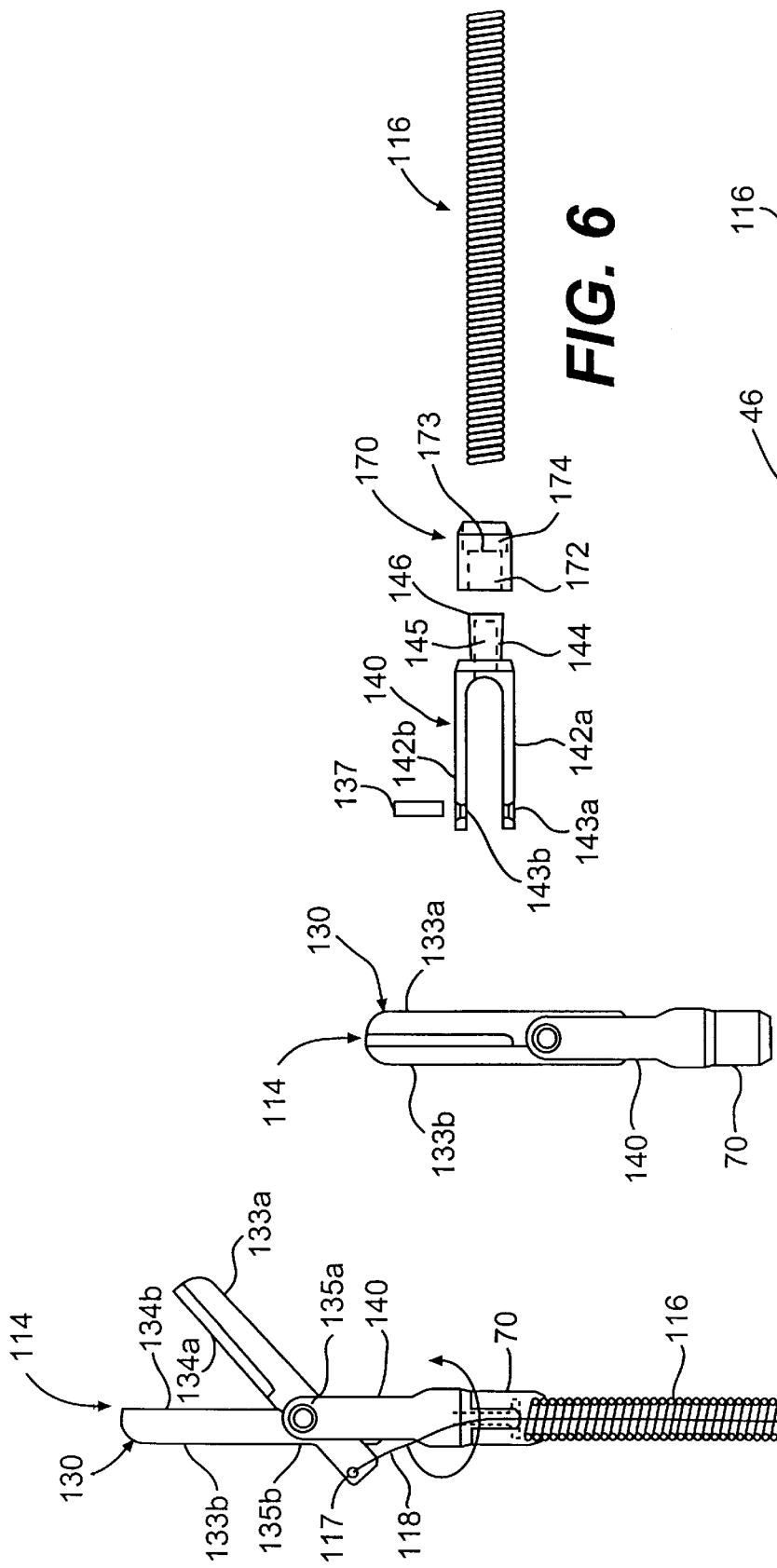

SURGICAL INSTRUMENT WITH A ROTATABLE DISTAL END

BACKGROUND OF THE INVENTION

1. Field of the Invention

The present invention relates to surgical instruments and, particularly, to an instrument with a rotatable distal end. Still more particularly, the present invention relates to an endoscopic instrument, such as scissors or a biopsy forceps device, with a rotatable distal end.

2. Background of Related Art

During many medical procedures, surgical instruments are commonly used in conjunction with other devices such as endoscopes, catheters, cannulas, and trocars. Typically, those devices provide the passageway for entry of the surgical instrument into the body. For example, a surgical procedure, such as biopsy tissue sampling, is often performed with an endoscope and an endoscopic surgical instrument within the endoscope. An endoscope is a long flexible tube carrying fiber optics. The fiber optics aid the physician in manipulating the endoscope to a site within the body and allow the physician to view that site during the procedure. The endoscope also has a lumen through which a surgical instrument may be inserted to perform some procedure at the body site. In the case of a biopsy, the surgical instrument is called a bioptome.

A bioptome typically includes a long flexible coil having a control wire extending therethrough. At its distal end, the bioptome has a pair of opposed jaws, while at its proximal end it has a manual actuator to actuate the jaws. Manipulation of the actuator opens and closes the jaws.

In order to take a biopsy tissue sample, the physician guides the endoscope to the biopsy site through a body lumen while viewing the passage of the endoscope and the biopsy site through the fiber optics. The bioptome is then inserted through the lumen of the endoscope until the jaws arrive at the biopsy site. While viewing the biopsy site, the physician positions the jaws around the tissue to be sampled and manipulates the actuator so that the jaws close around the tissue. A tissue sample is then cut or torn away from the surrounding tissue and trapped within the jaws of the bioptome. Keeping the jaws closed, the surgeon withdraws the bioptome from the endoscope and then opens the jaws to collect the biopsy tissue sample. If multiple tissue samples are desired a multiple sample bioptome, such as shown in U.S. Pat. No. 5,542,432, may be used.

During this sampling procedure, the desired tissue site may be difficult to reach or the jaws may arrive at the biopsy site in an unsuitable position or orientation for taking the desired tissue sample. The latter may occur because the jaws of the bioptome are not freely rotatable. In many bioptomes, torque applied at the proximal end of the bioptome does not translate into rotation of the jaws. Often, excessive manipulation of the endoscope is required to achieve any rotation of the jaws. Such manipulation can cause trauma to the patient.

Likewise, with many other surgical instrument tools, such as, for example, scissor blades, graspers, suture graspers, tissue manipulators, and forceps, torque applied at the proximal end of the instrument does not translate into rotation of the tool. Again, excessive manipulation of the instrument may be required to achieve any rotation of the tool causing trauma to the patient.

SUMMARY OF THE INVENTION

It is therefore an object of the invention to provide a surgical instrument that can be positioned easily around a tissue sample without excessive manipulation.

It is a further object of the invention to provide a surgical instrument in which torque may be transmitted from the proximal end to the distal end resulting in a rotatable surgical instrument.

It is a still further object of the invention to provide a surgical instrument that has a freely and easily rotatable distal tip.

It is another object of the invention to provide a surgical instrument having end effectors that may be oriented easily and properly with respect to the tissue site.

Additional objects and advantages of the invention will be set forth in the description which follows and, in part, will be obvious from the description or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises a surgical instrument, having a proximal end and a distal end, including a proximal actuator assembly, a distal end effector assembly having a surgical tool and a first rotational engagement member, a hollow member extending between the actuator and the end effector assembly, and a control member extending through the hollow member. The control member has a proximal end connected to the actuator assembly, a distal end connected to the end effector assembly, and a second rotational engagement member. In operation, actuation of the actuator assembly causes the control member to actuate the surgical tool, and the first engagement member engages the second engagement member to transmit torque applied to the control member to the end effector assembly.

The present invention also comprises a rotatable surgical instrument, having a proximal end and a distal end, including an extended hollow member, an end effector located at the distal end of the extended hollow member having an actuatable surgical tool; a control member extending through the hollow member and connected at its distal end to the end effector to actuate the surgical tool, and torque transmitting means located at the distal end of the instrument for transmitting torque from the control member to the end effector. The torque transmitting means fixes the control member rotationally relative to the end effector while allowing the control member to move axially relative to the end effector to actuate the end effector.

The present invention further comprises a rotatable endoscopic bioptome including an extended hollow member having a proximal end and a distal end, an end effector located at the distal end of the of the extended hollow member, and a control member extending through the hollow member and connected at its distal end to the end effector to actuate the end effector. The end effector includes an actuatable surgical tool and first engaging members disposed thereon. The control member has second engaging members corresponding to the first engaging members on the end effector. The second engaging members engage the first engaging members to permit relative axial movement between the control member and the end effector to actuate the end effector and to cause rotation of the surgical tool when torque is applied to the control member.

It is to be understood that both the foregoing general description and the following detailed description are exemplary and explanatory and are not restrictive of the invention as claimed.

BRIEF DESCRIPTION OF THE DRAWINGS

The accompanying drawings are included to provide a further understanding of the invention and are incorporated in and constitute a part of this specification. The drawings illustrate embodiments of the invention and, together with the description, serve to explain the principles of the invention.

FIG. 5a is a partial side view of a distal end of an endoscopic scissors according to an embodiment of the present invention.

FIG. 5b is a partial side elevation view of the distal end of FIG. 5a.

FIG. 6 is an expanded side view of a portion of the distal end of FIG. 5a.

FIG. 7 is a side view of a portion of the distal end of the of FIG. 5a.

DESCRIPTION OF THE PREFERRED EMBODIMENTS

Figure 1:
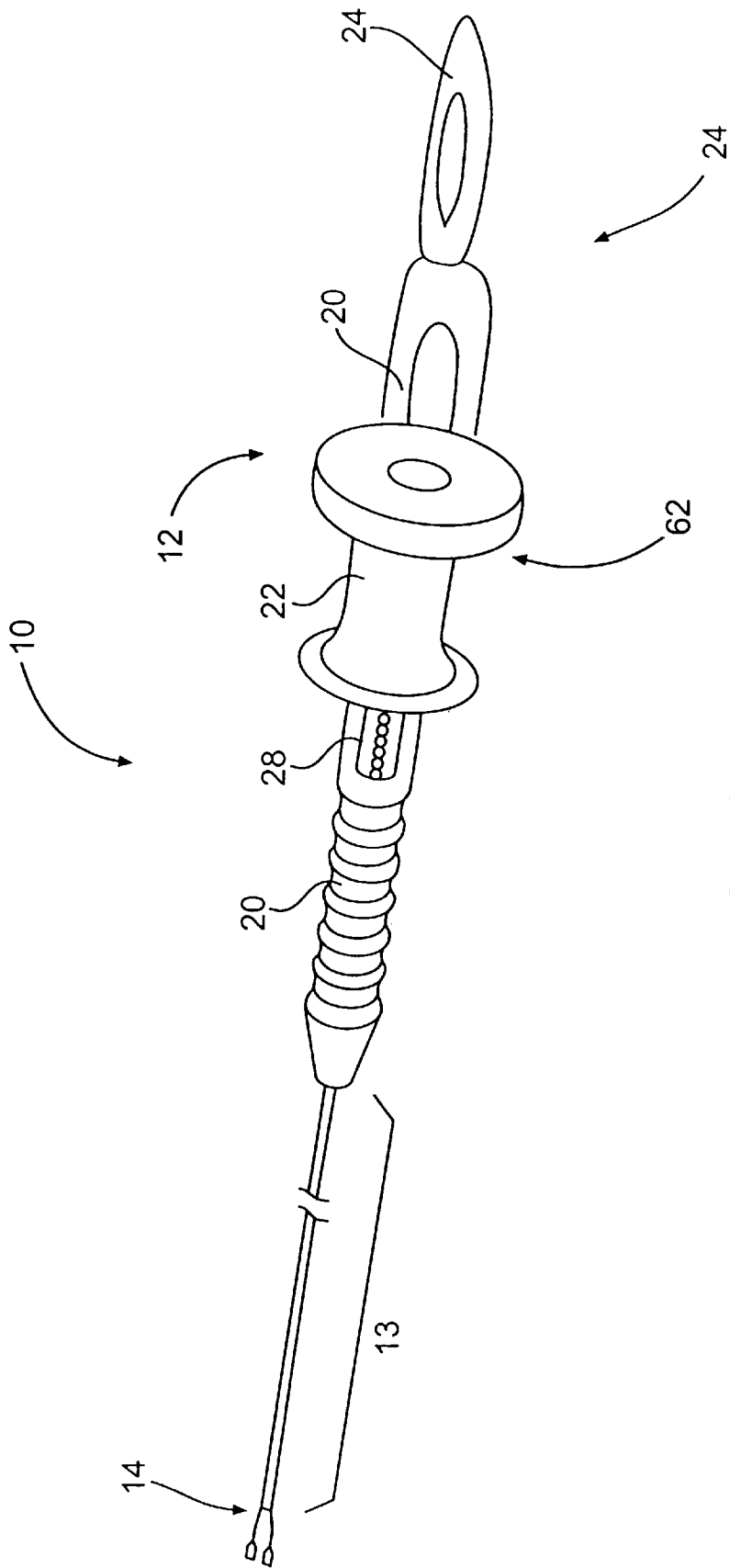
FIG. 1 is a side elevation view of an endoscopic bioptome according to a preferred embodiment of the present invention.

Reference will now be made in detail to the present preferred embodiments of the invention, examples of which are illustrated in the accompanying drawings. Wherever possible, the same reference numbers are used in the drawings and the description to refer to the same or like parts.

The present invention is directed to a surgical instrument, particularly an endoscopic bioptome, having a rotatable distal end. The instrument described in detail below includes engaging members disposed between the control wire and the end effector of the instrument. Any torque applied to the control wire is transmitted to the end effector through the engaging members causing rotation of the end effector thereby allowing easier and improved positioning of the instrument about a tissue sample.

While this invention will be described in connection with an endoscopic surgical instrument, and particularly an endoscopic bioptome and an endoscopic scissors, it is not limited to such. This invention is applicable to any surgical instrument requiring rotation at the distal end and any such surgical instrument used alone or in conjunction with other devices such as, but not limited to, catheters, cannulas, trocars, or any other tube like structures which allow the passage of an instrument into the body. Moreover, this invention is not limited to use in connection with the specific scissor assembly or jaw assembly described below. The use of other end effectors such as grasper, forceps, tissue manipulators, and suture graspers is within the scope of the invention.

Figure 2:
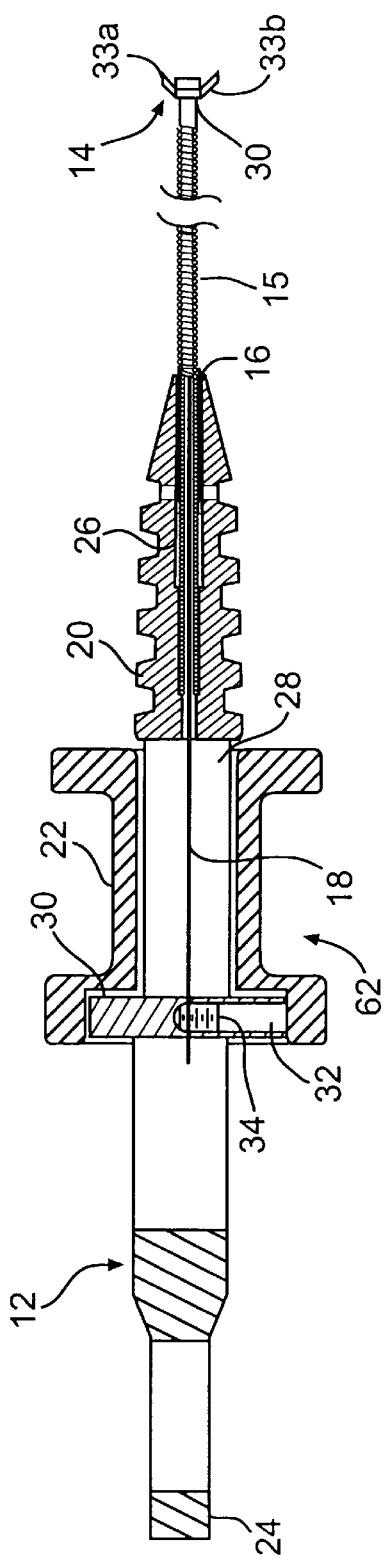
FIG. 2 is a sectional side view of the bioptome shown in FIG. 1.

FIGS. 1 and 2 show an endoscopic bioptome 10 according to an embodiment of the present invention. Bioptome 10 generally includes three main sections: a handle 12 at its proximal end; an end effector assembly 14 at its distal end; and a long, tube-like section 13 extending between handle 12 and end effector assembly 14. As shown in FIG. 2, a control wire 18 extends from handle 12, through section 13, to end effector assembly 14. In this embodiment, end effector 14 includes a jaw assembly 30 having a pair of opposed jaw cups 33a, 33b for taking a biopsy tissue sample. Handle 12 includes an actuator assembly 62. As will be described in more detail below, manipulation of actuator assembly 62 causes relative movement of control wire 18 and tube-like section 13 thereby actuating end effector 14.

Tube-like section 13 is generally comprised of a long and hollow coil 16. It should be recognized, however, that other tube-like structures, such as polymer tubing, braided polymeric tubing, or superelastic tubing could be used. Coil 16 is preferably flexible so that it may pass through the lumen of an endoscope. In other applications, however, such as with use in a trocar, flexibility of coil 16 may not be necessary or desired. Coil 16 is also preferably substantially longitudinally inelastic because end effector 14 is actuated as a result of relative axially movement between coil 16 and control wire 18. Coil 16 may be formed by wrapping the wire coil around a mandrel or by other suitable means. The size of coil 16 should be such that it fits within handle 12 and allows passage of control wire 18. Preferably, coil 16 is made from flat wire approximately 0.008 inches thick and 0.020 inches wide or from round wire approximately 0.021 inches in diameter. Coil 16 may be made from any suitable material that is highly flexible such as stainless steel. Alternatively, if flexibility is not required, the coil may still be made from stainless steel, or a polymer (liquid crystal) or other suitable material.

An outer sleeve 15 covering substantially the entire length of coil 16 may be provided. Sleeve 15 may increase the longitudinally inelastic nature of coil 16, add a degree of protection to coil 16, and lessen the friction between coil 16 and the lumen of the endoscope. Sleeve 15 is preferably formed from heat shrink tubing made of PTFE, FEP, polyolefin, or other suitable material that permits coil 16 to have enough flexibility to pass through the lumen of an endoscope. Preferably, sleeve 15 is integrally connected to coil 16, such that coil 16 does not slide within sleeve 15. Sleeve 15 may be applied to coil 16 by heat or other appropriate methods.

As with coil 16, control wire 18 is preferably flexible but substantially longitudinally inelastic. Ideally, control wire 18 is formed from 304 steel wire having an outer diameter of approximately 0.018 inches. It should be understood, however, that coil 16, sleeve 15, and control wire 18 could be formed from other suitable sizes and types of materials, or by other suitable manufacturing methods.

The handle assembly for use with the present invention may be any one that provides for relative movement between coil 16 and control wire 18. Handle 12 generally includes a main housing 20 and actuator assembly 62. Housing 20 and actuator 62 each secure one of coil 16 and control wire 18 so that relative movement of actuator 62 and housing 20 causes relative movement of coil 16 and control wire 18. For example, control wire 18 may be connected to actuator assembly 62 and coil 16 may be connected to housing 20 as shown in FIG. 2 and disclosed in U.S. Pat. No. 5,133,727, the complete disclosure of which is incorporated herein by reference. As shown in FIG. 2, housing 20 has a central longitudinal bore 26 and thumb ring 24. A slot 28 extends proximally from bore 26 to thumb ring 24. Actuator assembly 62 includes an axially displaceable spool 22 surrounding housing 20. Spool 22 includes a cross member 30 which passes through slot 28 in housing 20. Cross member 30 has a hole 32 and a radially engaging set screw 34.

Figure 3:
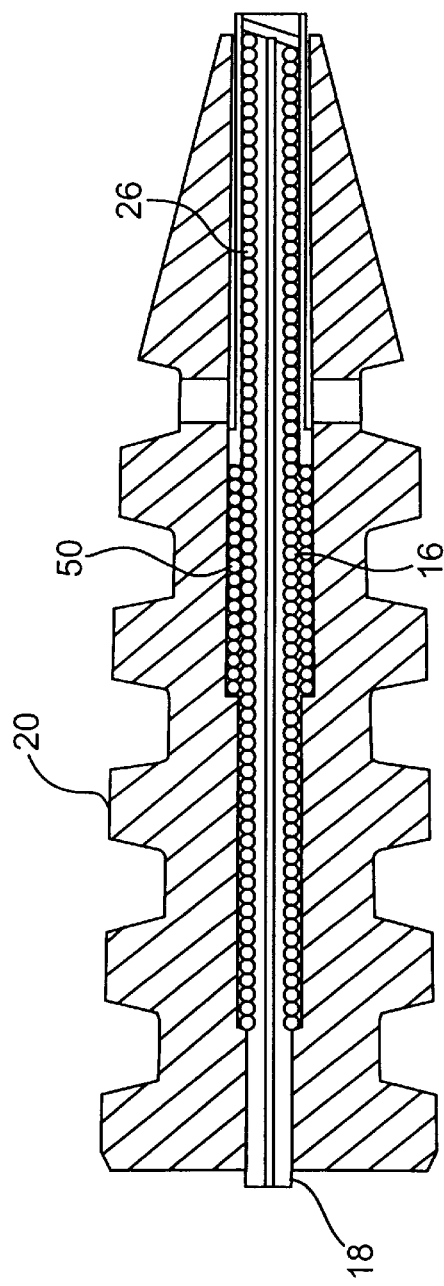
FIG. 3 is a sectional side view of a portion of the bioptome shown in FIG. 2.

The proximal end of coil 16 extends into and is secured within bore 26 by a locking coil 50 as shown in FIG. 3. Locking coil 50 has an inner diameter slightly less than the outer diameter of coil 16 to fix coil 16 in place. The proximal end of control wire 18 extends through coil 16 and bore 26 into slot 28 where it passes through hole 32 in cross member 30. Control wire 18 is secured within hole 32 by set screw 34. Coil 16 and control wire 18 could also be secured by other conventional means such as by adhesives or insert molding.

Figure 4:
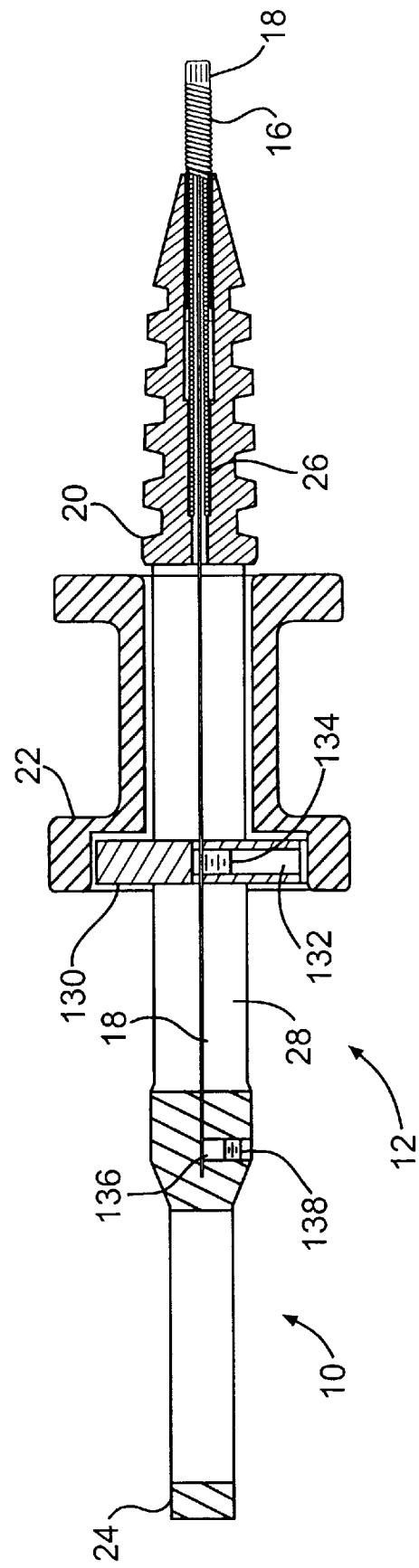
FIG. 4 is a sectional side view of the proximal end of the bioptome according to an embodiment of the present invention.

Alternatively, coil 16 could be connected to actuator assembly 62 and control member 18 could be connected to housing 20 as shown in FIG. 4 and disclosed in U.S. Pat. No. 5,542,432, the complete disclosure of which is incorporated herein by reference. In this example, the proximal end of coil 16 extends into bore 26 and slot 28 and into a hole 132 in a cross member 130 in actuator assembly 62. Coil 16 is fixed in hole 132 by a set screw 134. The proximal end of control wire 18 may extend through the longitudinal bore 26 and slot 28 and into a hole 136 in housing 20. Control wire 18 is fixed in hole 136 by set screw 138.

A distal end of another type of surgical instrument according to the present invention is shown in FIGS. 5a, 5b, 6, and 7. This type of distal end structure can be used in connection with the handle and coil assembly of the bioptome of FIGS. 1–4. In this embodiment, an end effector assembly 114 includes a scissor assembly 130 and a clevis assembly 140 for connecting scissor assembly 130 to a control wire 118. Scissor assembly 130 may have a pair of opposed scissor blades 133a and 133b. Each scissor blade 133a, 133b has a mounting hole 135a, 135b to connect scissor assembly 130 to clevis assembly 140. Each scissor blade 133a, 133b has a sharpened edge 134a, 134b for cutting. In the embodiment shown in FIG. 5a, scissor blade 133a is pivotable about the mounting holes, and scissor blade 133b is fixed so as not to pivot about the mounting holes. It should be recognized, however, that scissor blade 133b could also be pivotable. It should also be recognized that other surgical instruments, such as the jaw assembly of the bioptome shown in connection with FIGS. 1–4, graspers, or forceps could be mounted on clevis assembly 140 in place of the scissor assembly shown.

As shown in FIGS. 6 and 7, clevis assembly 140 has a pair of arms 142a, 142b at its distal end for connection to scissor assembly 130 and a stem 144 at its proximal end for receiving control wire 118. Each arm 142a, 142b has an axle hole 143a, 143b to correspond with mounting holes 135a, 135b on scissor blades 133a, 133b. Scissor blades 133a, 133b are mounted on arms 142a, 142b by an axle 137 extending through axle holes 143a, 143b and mounting holes 135a, 135b.

Clevis assembly 140 is connected to a coil 116 through a bushing 170. Bushing 170 has a bore 172 adapted to receive stem 144 of clevis 140 and a bore 174 adapted to receive coil 116. Coil 116 is fixedly retained in bore 174 through adhesives or other retaining means. Stem 144 is retained in bore 172 by way of a flared portion 146 on stem 144. Flared portion 146 abuts an edge 173 of the interface between bore 172 and bore 174. When flared portion 146 contacts edge 173, axial movement of clevis 140 is constrained. Clevis 140, however, is free to rotate within bushing 170. Bushing 170, alternatively, could be provided with a groove for receiving flared portion 146. Relative rotatory movement would also be allowed while axial motion would be constrained.

Control wire 118 extends through a passageway 145 in stem 144 into the space between clevis arms 142a, 142b. In the embodiment shown in FIG. 5a, control wire 118 is connected to scissor blade 133b through a hole 117 on scissor blade 133a. When assembled, manipulation of an actuator assembly, such as actuator assembly 62 shown in FIGS. 1–4, causes axial movement of control wire 118 relative to coil 116 and clevis assembly 140 resulting in movement of scissor blade 133a. The movement of scissor blade 133a from a closed position to an open position is shown in FIGS. 5b and 5a. In the embodiment shown, scissor blade 133b remains stationary while opposing scissor blade 133a is pivotable about axle 137. It should be recognized, however, that other connections of control wire 118 to end effector 114 are within the scope of the invention, including a connection which allows both opposing blades, or other instrument, to pivot. For instance, the dual control wire arrangement shown in U.S. Pat. No. 5,133,727 could be used, or a single guide wire could be connected to both elements of the end effector through a linking mechanism as shown in, for example, U.S. Pat. No. 5,141,519, or U.S. Pat. No. 5,171,258.

According to the present invention, stem 144 of clevis 140 engages the distal end of control wire 118 such that torque applied to the proximal end of control wire 118 will be transmitted to scissor assembly 130 causing it to rotate while at the same time allowing axial movement of control wire 118 relative to stem 144 of clevis 140 to actuate the scissor assembly. Control wire 118 and stem 144 are therefore provided with appropriate structure that engage to provide this transmission of torque. More particularly, first and second engaging members are respectively provided on the inner surface of passageway 145 and at least the distal end of control wire 118.

Figure 9:
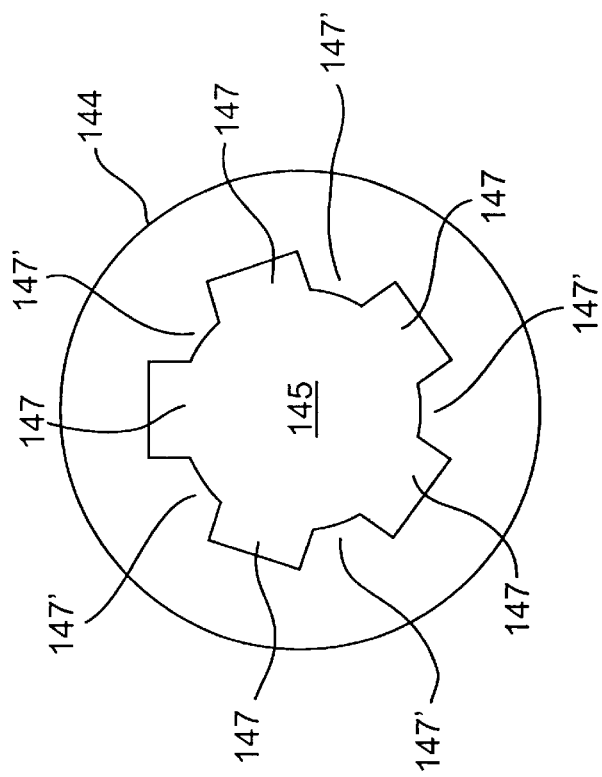
FIG. 9 is a sectional end view of a portion of a distal end of an endoscopic instrument according to an embodiment of the present invention.
Figure 8:
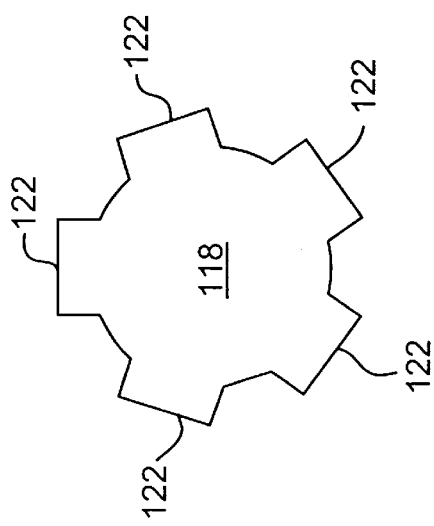
FIG. 8 is sectional end view of the distal end of a control wire according to an embodiment of the present invention.

As shown in FIGS. 8 and 9, the first engaging members are preferably longitudinally splined recesses 147 defined by surface portion 147', and the second engaging members are preferably longitudinal splines 122. Splines 122 correspond to recesses 147 and engage surface 147' when the distal end of control wire 118 passes through passageway 145. When torque is applied to the proximal end of control wire 118, the engagement of splines 122 and surface 147' in passageway 145 causes rotation of stem 144, and therefore clevis 140, and scissor assembly 130. This permits the end effector assembly, particularly scissor blades 133a, 133b or jaw cups 33a, 33b, to rotate into a desired angular position. At the same time, splines 142 and recesses 147 do not restrict the movement of control wire 118 axially relative to stem 144 for actuation the end effectors, that is scissor blades 133a, 133b or jaw cups 33a, 33b.

Figure 11:
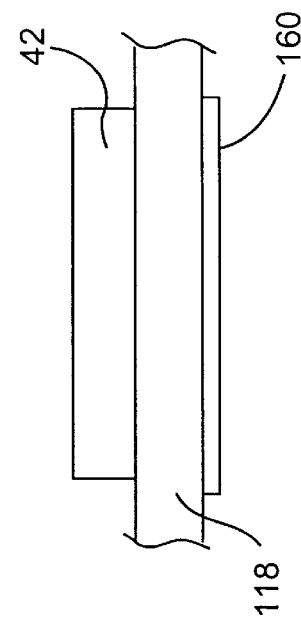
FIG. 11 is a partial sectional side view of the distal end of the control wire shown in FIG. 10 taken along line I—I of FIG. 10
Figure 10:
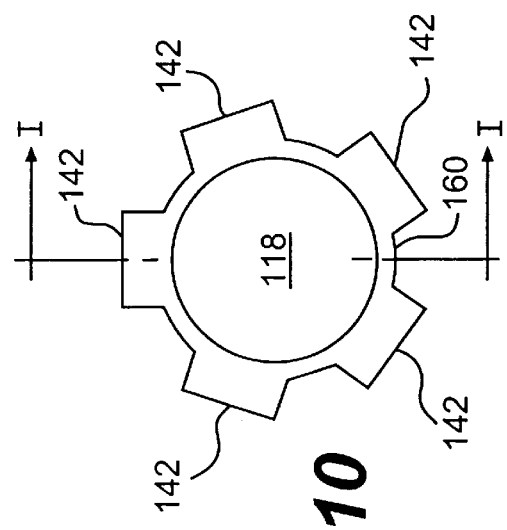
FIG. 10 is an end view of a control wire according to an embodiment of the present invention.

In a preferred embodiment, the second engaging members are provided on the distal end of control wire 118 by a sleeve 160 as shown in FIGS. 10 and 11. The outer surface of sleeve 160 may be provided with longitudinal splines shown at 142, and sleeve 160 may be attached to control wire 118 by any suitable method such as with adhesives. In this embodiment, passageway 145 in stem 144 matingly receives control wire 118 and sleeve 160.

Splines 122, or 142 in the embodiment of FIGS. 10 and 11, may cover the entire distal end of control wire 118 or any length in between. Preferably, however, splines 122 or 142 are at least as long as the length of displacement of control wire 118 during a stroke required to actuate scissor assembly 130 or other end effector. This ensures that at least a portion of the splines 122 or 142 remain in passageway 45 during operation of the instrument and actuation of the end effector. It should be recognized, however, that varying the length of the splines 122 or 142 or the length of sleeve 160 is within the scope of the invention. In addition, while this invention has been described in connection with longitudinal splines, any other suitable structure that transmits torque to the distal end of the instrument while still permitting relative axial movement between the control wire and the outer coil is within the scope of the invention.

It will be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the following claims and their equivalents.

What is claimed is:

1. A surgical instrument having a proximal end and a distal end, the instrument comprising:
   a proximal actuator assembly;
   a distal end effector assembly having a surgical tool and a first rotational engagement member;
   a hollow member extending between the actuator and the end effector assembly; and
   a control member extending through the hollow member, the control member having a proximal end connected to the actuator assembly, a distal end connected to the end effector assembly, and a second rotational engagement member, wherein actuation of the actuator assembly causes the control member to actuate the surgical tool and wherein the first engagement member engages the second engagement member to transmit torque applied to the control member to the end effector assembly, while allowing relative axial movement between the first and second engagement members.

2. The surgical instrument according to claim 1, wherein the end effector includes a base connected to the tool, the base having a passageway therethrough for receiving the distal end of the control member.

3. The surgical instrument according to claim 2, wherein the first engagement member comprises the surface of the passageway of the base defining longitudinally recessed splines, and the second engagement member includes longitudinal splines disposed on the distal end of the control member, the longitudinal splines engaging the surface of the passageway when torque is applied to the control member causing the end effector to rotate.

4. The surgical instrument according to claim 3, wherein the longitudinal splines comprise a sleeve attached to the distal end of the control member, the sleeve having splines on the outside surface thereof.

5. The surgical instrument according to claim 3, wherein the control member is displaced axially relative to the base of the end effector during actuation of the end effector and wherein the longitudinal splines are at least as long as the length of displacement of the control member during actuation of the end effector.

6. The surgical instrument according to claim 1, wherein the surgical tool is a pair of opposed jaws.

7. The surgical instrument according to claim 1, wherein the proximal actuator assembly includes a handle and an actuation member displaceable relative to the handle.

8. The surgical instrument according to claim 7, wherein the hollow member is connected to the handle and the control member is connected to the actuation member such that displacement of the actuation member relative to the handle causes displacement of the control member relative to the hollow member.

9. The surgical instrument according to claim 7, wherein the control member is attached to the handle and the hollow member is attached to the actuation member so that displacement of the actuation member relative to the handle causes displacement of the hollow member relative to the control member.

10. A rotatable surgical instrument having a proximal end and a distal end, the instrument comprising:
    an extended hollow member;
    an end effector located at the distal end of the extended hollow member, the end effector including a base and an actuatable surgical tool;
    a control member having a proximal end and a distal end, the control member extending through the hollow member and connected at the distal end to the end effector to actuate the surgical tool; and
    a first torque transmitting member located at the base of the end effector and a second torque transmitting member located on the control member for transmitting torque from the control member to the end effector, wherein the first and second torque transmitting members fix the control member rotationally relative to the end effector while allowing the control member to move axially relative to the base of the end effector when the end effector is actuated.

11. The surgical instrument according to claim 10, wherein torque applied to the control member is transmitted to the end effector through the first and second torque transmitting members.

12. The surgical instrument according to claim 11, wherein the base has a passageway therethrough for receiving the control member, and wherein the first torque transmitting member comprises the surface of the passageway defining longitudinally recessed splines.

13. The surgical instrument according to claim 12, wherein the second torque transmitting member includes longitudinal splines disposed on the distal end of the control member, the longitudinal splines engaging the surface of the passageway when torque is applied to the control member causing the end effector to rotate.

14. The surgical instrument according to claim 13, wherein the longitudinal splines comprise a sleeve attached to the distal end of the control member, the sleeve having splines on the outside surface thereof.

15. The surgical instrument according to claim 13, wherein the control member is displaced axially relative to the base of the end effector during actuation of the end effector, and wherein the longitudinal splines are at least as long as the length of displacement of the control member during actuation of the end effector.

16. The surgical instrument according to claim 10, wherein the surgical tool is a pair of opposed scissor blades.

17. The surgical instrument according to claim 10, further including an actuator assembly connected to the proximal end of the control member for actuating the end effector.

18. The surgical instrument according to claim 17, wherein the actuator assembly includes a handle and an actuation member displaceable relative to the handle.

19. The surgical instrument according to claim 18, wherein the hollow member is connected to the handle and the control member is connected to the actuation member such that displacement of the actuation member relative to the handle causes displacement of the control member relative to the hollow member.

20. The surgical instrument according to claim 18, wherein the control member is attached to the handle and the hollow member is attached to the actuation member so that displacement of the actuation member relative to the handle causes displacement of the hollow member relative to the control member.

21. A rotatable endoscopic bioptome comprising:
   an extended hollow member having a proximal end and a distal end;
   an end effector, located at the distal end of the of the extended hollow member, the end effector including an actuatable surgical tool and first engaging members disposed thereon; and
   a control member extending through the hollow member, the control member connected at a distal end to the end effector to actuate the end effector, the control member having second engaging members corresponding to the first engaging members on the end effector, wherein the second engaging members engage the first engaging members to permit relative axial movement between the control member and the end effector to actuate the end effector and to cause rotation of the surgical tool when torque is applied to the control member.

22. The surgical instrument according to claim 21, wherein the end effector includes a base connected to the tool, the base having a passageway therethrough for receiving the distal end of the control member.

23. The surgical instrument according to claim 22, wherein the first engagement member comprises the surface of the passageway of the base defining longitudinally recessed splines, and the second engagement member includes longitudinal splines disposed on the distal end of the control member, the longitudinal splines engaging the surface of the passageway when torque is applied to the control member causing the end effector to rotate.

24. The surgical instrument according to claim 23, wherein the longitudinal splines comprise a sleeve attached to the distal end of the control member, the sleeve having splines on the outside surface thereof.

25. The surgical instrument according to claim 23, wherein the longitudinal splines are at least as long as the length of displacement of the control member during actuation of the end effector.

26. The surgical instrument according to claim 21, wherein the surgical tool is a pair of opposed jaws.

27. The surgical instrument according to claim 21, further including an actuator assembly connected to a proximal end of the control member for actuating the end effector.

28. The surgical instrument according to claim 27, wherein the actuator assembly includes a handle and an actuation member displaceable relative to the handle.

29. The surgical instrument according to claim 28, wherein the hollow member is connected to the handle and the control member is connected to the actuation member such that displacement of the actuation member relative to the handle causes displacement of the control member relative to the hollow member.

30. The surgical instrument according to claim 28, wherein the control member is attached to the handle and the hollow member is attached to the actuation member so that displacement of the actuation member relative to the handle causes displacement of the hollow member relative to the control member.

31. A surgical instrument having a proximal end and a distal end, the instrument comprising:
   a proximal actuator assembly;
   a distal end effector assembly having a surgical tool and a first rotational engagement member;
   a hollow member extending between the actuator and the end effector assembly; and
   a control member extending through the hollow member, the control member having a proximal end connected to the actuator assembly, a distal end connected to the end effector assembly, and a second rotational engagement member, wherein actuation of the actuator assembly causes the control member to actuate the surgical tool and wherein the first engagement member engages the second engagement member to transmit torque applied to the control member to the end effector assembly while allowing the end effector assembly to rotate relative to the hollow member.

32. The surgical instrument according to claim 31, wherein the end effector assembly includes a base connected to the tool, the base having a passageway therethrough for receiving the distal end of the control member.

33. The surgical instrument according to claim 32, wherein the first engagement member comprises the surface of the passageway of the base defining longitudinally recessed splines, and the second engagement member includes longitudinal splines disposed on the distal end of the control member, the longitudinal splines engaging the surface of the passageway when torque is applied to the control member causing the end effector assembly to rotate.

34. The surgical instrument according to claim 33, further comprising a sleeve attached to the distal end of the control member, wherein the longitudinal splines of the second engagement member are on the outside surface of the sleeve.

35. The surgical instrument according to claim 33, wherein the control member is displaced axially relative to the base of the end effector assembly during actuation of the end effector assembly and wherein the longitudinal splines are at least as long as the length of displacement of the control member during actuation of the end effector assembly.

* * * * *

UNITED STATES PATENT AND TRADEMARK OFFICE
CERTIFICATE OF CORRECTION

PATENT NO. : 6,027,522
DATED : February 22, 2000
INVENTOR(S) : Matthew Palmer

It is certified that error appears in the above-indentified patent and that said Letters Patent is hereby corrected as shown below:

In Claim 21, Col. 9, line 13, delete "of the" (second occurrence).

Signed and Sealed this

Twenty-seventh Day of February, 2001

Attest:

NICHOLAS P. GODICI

Attesting Officer     Acting Director of the United States Patent and Trademark Office